United States Patent [19]

Theissen

[11] Patent Number: 4,599,442

[45] Date of Patent: Jul. 8, 1986

[54] (BISALKOXYCARBONYL)ALKYL 5-[2-CHLORO-4-(TRIFLUOROMETHYL)-PHENOXY]-2-NITROBENZOATES

[75] Inventor: Robert J. Theissen, Bridgewater, N.J.

[73] Assignee: Rhone-Poulenc, Inc., Monmouth Junction, N.J.

[21] Appl. No.: 282,203

[22] Filed: Jul. 10, 1981

Related U.S. Application Data

[63] Continuation-in-part of Ser. No. 274,105, Jun. 16, 1981, which is a continuation-in-part of Ser. No. 117,753, Feb. 1, 1980, abandoned.

[51] Int. Cl.$^4$ .............................................. C07C 79/46
[52] U.S. Cl. ......................................... 560/21; 71/108
[58] Field of Search ..................... 560/21; 71/108, 107

[56] References Cited

U.S. PATENT DOCUMENTS

| 2,765,224 | 10/1956 | Lambrech | 71/107 |
| 2,818,424 | 12/1957 | Zeile et al. | 71/108 |
| 3,499,008 | 3/1970 | Talet et al. | 71/107 |
| 3,928,416 | 12/1975 | Bayer et al. | 560/21 |
| 3,979,437 | 9/1976 | Theissen | 560/21 |
| 4,134,753 | 1/1979 | Horlein et al. | 71/108 |
| 4,140,520 | 2/1979 | Nishiyama et al. | 71/108 |
| 4,400,530 | 8/1983 | Grove | 560/21 |

FOREIGN PATENT DOCUMENTS

| 0033629 | 8/1981 | European Pat. Off. | 560/21 |
| 2805981 | 8/1979 | Fed. Rep. of Germany | 71/108 |
| 47-62637 | 10/1972 | Japan | 71/108 |

OTHER PUBLICATIONS

Nishiyama et al II, "Phenoxyphenoxymethyl, etc.,"(1978).
CA 89 No. 42,773x (1978).

Primary Examiner—Glennon H. Hollrah
Attorney, Agent, or Firm—Morgan, Finnegan, Pine, Foley & Lee

[57] ABSTRACT

There is provided herbicidal (bisalkoxycarbonyl)alkyl 5-[2-chloro-4-(trifluoromethyl)phenoxy]-2-nitrobenzoates. These compounds are particularly useful when applied in a post-emergence application to soybean fields containing broadleaf weeds.

3 Claims, No Drawings

(BISALKOXYCARBONYL)ALKYL 5-[2-CHLORO-4-(TRIFLUOROMETHYL)PHENOXY]-2-NITROBENZOATES

CROSS REFERENCE TO RELATED APPLICATIONS

This application is a continuation-in-part of U.S. application Ser. No. 274,105, filed June 16, 1981, which in turn is a continuation-in-part of U.S. application Ser. No. 117,753, filed Feb. 1, 1980 now abandoned.

BACKGROUND OF THE INVENTION

The invention is concerned with herbicidal(bisalkoxycarbonyl)-alkyl 5-[2-chloro-4-(trifluoromethyl)-phenoxy]-2-nitrobenzoates.

The compound, 5-[2-chloro-4-(trifluoromethyl)-phenoxy]-2-nitrobenzoic acid, including the salt forms thereof, is known to have herbicidal activity. According to a particular herbicidal treatment, it has been proposed to apply this compound in a post-emergence fashion to control weeds, especially broadleaf weeds, in soybean fields. Accordingly, in such an application, a herbicide must possess the following two properties at the applied dosage rate: (1) the ability to control the target weeds; and (2) the ability to remain safe to the soybeans.

In attempting to improve on the herbicidal properties of 5-[2-chloro-4-(trifluoromethyl)phenoxy]-2-nitrobenzoic acid and salts thereof, various derivatives of these compounds have been proposed including alkyl and cycloalkyl esters, alkylthio esters, phenyl ester, alkyl and dialkyl amido and benzoyl chloride forms. U.S. Patents which describe such compounds and the like include Nos. 3,652,645; 3,784,635; 3,873,302; 3,983,168; 3,907,866; 3,798,276; 3,928,416; and 4,063,929. For example, the simple methyl ester of the above-mentioned acid, i.e., methyl 5-[2-chloro-4-(trifluoromethyl)-phenoxy]-2-nitrobenzoate, has been proposed, and it has been discovered that this compound has even greater herbicidal activity than 5-[2-chloro-4-(trifluoromethyl)-phenoxy]-2-nitrobenzoic acid with respect to various weeds, e.g. broadleaf weeds. However, it has also been discovered that methyl 5-[2-chloro-4-(trifluoromethyl)-phenoxy]-2-nitrobenzoate has a relatively large degree of post-emergence herbicidal activity with respect to crops. Consequently, methyl 5-[2-chloro-4-(trifluoromethyl)phenoxy]-2-nitrobenzoate should not be applied in a post-emergence fashion to control broadleaf weeds in soybeans, because this compound tends to kill soybeans along with the weeds in such applications.

It has even been reported that the sodium salt of 5-[2-chloro-4-(trifluoromethyl)phenoxy]-2-nitrobenzoate tends to cause some initial damage to soybeans when applied in a postemergence fashion to control weed in soybean fields (see R. Y. Yih, "TODAY'S HERBICIDE: BLAZER TM-A New Postemergence Herbicide", Weeds Today, Vol. 12, No. 1, page 14, Early Spring 1981). Although the soybeans have been observed to recover from this initial damage, it would be desirable to develop compounds which give a lesser degree of initial soybean damage.

Accordingly, there is a need in the art for compounds which have a desirable combination of herbicidal properties with respect to weed activity and crop safety.

SUMMARY OF THE INVENTION

This invention provides certain herbicidal(bisalkoxycarbonyl)alkyl 5-[2-chloro-4-(trifluoromethyl)phenoxy]-2-nitrobenzoates. Particular examples of such compounds include those of the formula:

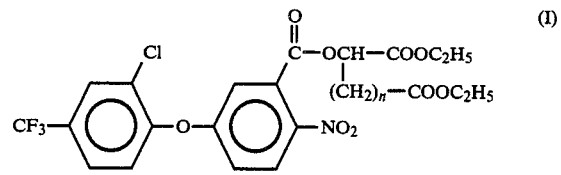

where n is zero or one.

The following compounds as defined by Formula I were prepared:

| Compound | n | m.p. °C. |
|---|---|---|
| 1 | 1 | oil |
| 2 | 0 | oil |

COMPOUND 1

Preparation of [1,2-bis-(ethoxycarbonyl)ethyl]5-[2-chloro-4-(trifluoromethyl)phenoxy)-2-nitrobenzoate.

To a stirred solution of 5-[2-chloro-4-(trifluoromethyl)phenoxy]-2-nitrobenzyl chloride (3.8 g, 0.01 mole) in acetone (10 ml) was successively added diethyl DL malate (1.9 g, 0.01 mole) in acetone (10 ml) and triethylamine (1.01 g, 0.01 mole) in acetone (5 ml). A white precipitate quickly formed. The reaction was heated to reflux for 24 hours. Upon cooling, the reaction was poured in water (75 ml) and extracted twice with methylene chloride (25 ml@). The combined organic extracts were successively washed with 5% sodium hydroxide and brine solutions. The dried solution was stripped of solvent to give 3.5 g of an amber oil.

IR(neat): C=O 1740 cm$^{-1}$ (broad

NMR(CDCl$_3$): triplet 1.38 ppm (6H, J=7.0 HZ), doublet 3.05 ppm (2H, J=6.0 HZ), 2 overlapping sets of quartets 4.0–4.5 ppm (4H), triplet 5.82 ppm (1H, J=6.0 HZ), complex multiplet 7.0–8.0 ppm (5H), doublet 8.20 ppm (1H, J=9.0 HZ)

COMPOUND 2

Preparation of bis-(ethoxycarbonyl)methyl 5-[2-chloro-4-(trifluoromethyl)phenoxy]-2-nitrobenzoate.

To a stirred solution of hydroxy diethylmalonate (0.47 g, 0.0026 mole) and pyridine (0.5 ml, 0.0053 mole) in toluene (100 ml) under a nitrogen atmosphere was added dropwise 5-[2-chloro-4-(trifluoromethyl)phenoxy]-2-nitrobenzoyl chloride (1.0 g, 0.002 mole) in toluene (15 ml). After 2 hours stirring at room temperature, the turbid solution was diluted with water and extracted with ether. The organic layer was washed twice with water, dried and the solvent removed to give 1.3 g of an oil.

IR(neat): C=O 1750 cm$^{-1}$ (broad)

The compounds of this invention can be applied in various ways to achieve herbicidal action. They can be applied per se, but are preferably applied as the toxic components in pesticidal compositions of the compound and a carrier. These compositions may be applied directly to the soil and often incorporated therewith. The compositions can be applied as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil.

In practice, herbicidal application is measured in terms of pounds of herbicide applied per acre. The compounds of this invention are effective herbcides when applied in herbicidal amounts, i.e., at rates between about 0.03 pound and about 10 pounds per acre.

HERBICIDAL EFFECTIVENESS

Method of Propagating Test Species

Crop and weed species are planted in 8"×10" disposable fiber flats containing potting soil to provide each flat with a 4" row of all test species. Crop species consist of field corn (CN), cotton (CT), and soybeans (SB). The weed species consist of foxtail millet (FM), green foxtail (GF), velvetleaf (VL), cocklebur (CB), wild mustard (WM) and pigweed (PW).

Cotton, corn, soybean, and cocklebur plantings consist of 4 to 5 seeds per row depending upon species. The smaller seeded species (velvetleaf, wild mustard, pigweed, foxtail millet and green foxtail) are planted in an uncounted but sufficient number to provide a solid row of seedlings.

Plantings for the pre- and post-emergence portions of the test are identical as to seeding. The initial watering until emergence is done from the top. The post-emergence phase is propagated in advance so as to provide plants of the proper stage of development at the time of treatment. Plantings for the pre-emergence phase are made not more than one day in advance of treatment.

The desired stage of development for treatment of the post-emergence broadleaf species (CT, SB, CB, VL, WM, PW) is the one true leaf or first trifoliate leaf stage. The desired stage for corn would be a height of 3-4", while a 2" height would be adequate for the grasses.

Method of Treatment

Spray applications are made with a handgun sprayer (aspirator type) simultaneously to one flat of established plants for the post-emergence phase and one newly seeded flat for the pre-emergence phase. A 10 lb./acre treatment rate consists of the uniform application of 116 milligrams of test compound to the combined area of the two flats (160 sq. inches). Application is made in a solvent mixture consisting of 40 ml acetone and 40 ml water and a surfactant concentration of 0.1 percent.

Following spray application, flats are returned to the greenhouse where watering of the post-emergence phase is done only by subirrigation. The pre-emergence phase is top watered by sprinkling until after test species have emerged. Subsequent watering is by subirrigation.

Two weeks after treatment, the pre- and post-emergence injury and control is rated on a 0-100 percent injury and control scale. Special physiological effects are rated as to intensity also at this time.

The herbicidal test data obtained in the above manner is reported for Compounds 1-2 and was obtained at application rates ranging from 2 lbs. down to ¼ lb/acre. The following lists metric equivalents for rates expressed in terms of lbs./acre.

| Application Rate | |
|---|---|
| US - lb./acre | Metric - kg/ha |
| 10.0 | 11.2 |
| 4.0 | 4.48 |
| 2.0 | 2.24 |
| 1.0 | 1.12 |
| 0.5 | 0.56 |
| 0.25 | 0.28 |
| 0.125 | 0.14 |
| 0.0625 | 0.07 |

Test results are set forth in Table I pre-emergence and post-emergence.

TABLE I

| Compound No. | Dosage Lbs./ Acre | Pre-Emergence | | | | | | | | | Post-Emergence | | | | | | | | |
|---|---|---|---|---|---|---|---|---|---|---|---|---|---|---|---|---|---|---|---|
| | | FM | GF | VL | CB | WM | PW | CT | CN | SB | FM | GF | VL | CB | WM | PW | CT | CN | SB |
| 1 | 2 | 40 | 10 | 60 | 10 | 90 | 100 | 10 | 0 | 0 | 100 | 100 | 100 | 100 | 100 | 100 | 100 | 90 | 60 |
| | ½ | 30 | 20 | 10 | 0 | 90 | 90 | 0 | 0 | 0 | 90 | 90 | 100 | 100 | 100 | 100 | 100 | 90 | 30 |
| | ¼ | 10 | 20 | 10 | 0 | 80 | 100 | 10 | 10 | 0 | 90 | 80 | 100 | 100 | 100 | 100 | 100 | 80 | 60 |
| 2 | 2 | 100 | 90 | 30 | 0 | 100 | 100 | 20 | 0 | 0 | 100 | 90 | 90 | 90 | 100 | 100 | — | 50 | 60 |
| | 1 | 90 | 70 | 20 | 0 | 90 | 100 | 10 | 10 | 0 | 100 | 80 | 90 | 70 | 100 | 90 | — | 40 | 50 |
| | ½ | 90 | 40 | 20 | 0 | 70 | 100 | 10 | 0 | 0 | 90 | 80 | 70 | 70 | 100 | 90 | — | 20 | 30 |
| | ¼ | 70 | 10 | 10 | 0 | 40 | 90 | 0 | 0 | 10 | 60 | 70 | 60 | 60 | 100 | 90 | — | 20 | 20 |

Compound I was also tested for post-emergence activity under field conditions along with sodium 5-[2-chloro-4-(trifluoromethyl)phenoxy]-2-nitrobenzoate (Compound A). These field tests were conducted as follows.

Field test plots (14' w×60' l) were seeded lengthwise with the following:

Crops:
   Soybean, cotton, wheat, barley and rice
Weeds:
   green foxtail, barnyard grass, annual morningglory, velvetleaf, pigweed, wild mustard, and cocklebur Treatments were applied 5 weeks after planting with a log sprayer beginning at 1.0 lb A.I.; observations were made at 1.0, 0.5, 0.25 and 0.125 lb rates. Weed control was observed at 13 and at 28 days after treatment, using a rating scale of 0 to 100.

Compound 1 was formulated as a 2 lb/gal emulsifiable concentrate in mixed xylenes containing 7.3 wt % of Sporto 234 emulsifier. Compound A was formulated as a 2 lb/gal aqueous solution without any adjuvants.

The results of these field tests are set forth in Table II. In this table BG stands for barnyard grass and MG stands for morningglory.

TABLE II

| Cpd No. | lbs./acre | % Grass Control @ 13 Days | | % Grass Control @ 28 Days | | % Broadleaf Control @ 13 Days | | | | | % Broadleaf Control @ 28 Days | | | | | % Crop Injury @ 5 Days |
| --- | --- | --- | --- | --- | --- | --- | --- | --- | --- | --- | --- | --- | --- | --- | --- | --- |
| | | GF | BG | GF | BG | MG | VL | PW | WM | CB | MG | VL | PW | WM | CB | SB |
| 1 | 1 | 27 | 13.8 | 31.2 | 15.0 | 96.5 | 100 | 100 | 100 | 85.0 | 95.0 | 98.8 | 100 | 100 | 94.5 | 26.5 |
| | ½ | 17.5 | 3.8 | 18.8 | 0 | 78.7 | 100 | 92.8 | 938 | 66.7 | 85.0 | 96.7 | 99.5 | 92.5 | 76.7 | 17.0 |
| | ¼ | 7.5 | 1.3 | 17.5 | 0 | 91.7 | 77.3 | 88.8 | 86.3 | 41.7 | 76.5 | 63.0 | 90.0 | 66.2 | 34.7 | 8.2 |
| | ⅛ | 5.0 | 0 | 12.5 | 0 | 36.7 | 57.3 | 70.0 | 73.8 | 41.7 | 55.0 | 47.0 | 61.2 | 26.2 | 23.8 | 4.5 |
| A | 1 | 91.5 | 42.5 | 94.2 | 42.5 | 96.5 | 100 | 100 | 100 | 98.0 | 91.0 | 81.2 | 100 | 100 | 97.5 | 42.5 |
| | ½ | 52.5 | 22.5 | 78.8 | 16.2 | 95.2 | 91.2 | 97.8 | 100 | 92.5 | 87.7 | 72.5 | 93.8 | 100 | 76.5 | 33.8 |
| | ¼ | 30.0 | 12.5 | 45.0 | 8.8 | 75.0 | 63.8 | 92.8 | 99.0 | 72.0 | 56.0 | 48.0 | 87.0 | 100 | 57.5 | 27.2 |
| | ⅛ | 6.3 | 8.8 | 20.0 | 2.5 | 66.8 | 52.5 | 86.3 | 91.3 | 54.5 | 30.3 | 46.2 | 80.0 | 52.5 | 30.0 | 12.5 |

The compounds of the present invention may be particularly advantageous when used to control weeds in field of crops which are relatively tolerant thereto. For instance, the foregoing data demonstrates that certain crop species are more tolerant to these compounds than certain grass or broadleaf weed species. The herbicidal compounds of the present invention are particularly useful when applied in post-emergence applications to control broadleaf weeds, e.g., morningglory, velvetleaf, cocklebur, wild mustard and pigweed, in soybean fields.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A herbicidal compound of the formula

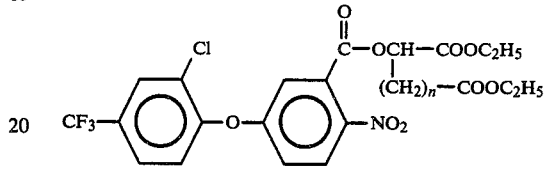

where n is zero or one.

2. A herbicidal compound according to claim 1 of the formula

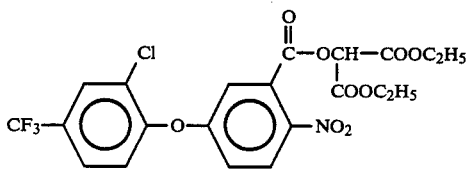

3. A herbicidal compound according to claim 1 of the formula

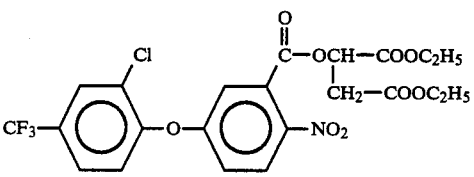

* * * * *